United States Patent [19]

Savage et al.

[11] Patent Number: 4,801,753
[45] Date of Patent: Jan. 31, 1989

[54] BIOLOGICALLY ACTIVE TRICYCLIC COMPOUNDS AND PHARMACEUTICAL COMPOSITIONS CONTAINING SAME

[75] Inventors: David S. Savage, Glasgow; Thomas Sleigh, Wishaw; John K. Clark, Hamilton, all of Scotland

[73] Assignee: Akzona Incorporated, Asheville, N.C.

[21] Appl. No.: 98,203

[22] Filed: Sep. 17, 1987

Related U.S. Application Data

[63] Continuation of Ser. No. 886,489, Sep. 8, 1986, abandoned, which is a continuation of Ser. No. 772,478, Oct. 4, 1985, abandoned, which is a continuation of Ser. No. 545,797, Oct. 26, 1983, abandoned, which is a continuation of Ser. No. 348,371, Feb. 10, 1982, abandoned, which is a continuation of Ser. No. 842,882, Oct. 17, 1977, abandoned.

[30] Foreign Application Priority Data

Oct. 27, 1976 [GB] United Kingdom ............... 44675/76

[51] Int. Cl.⁴ ..................... A61K 31/135; C07C 87/64
[52] U.S. Cl. ...................................... 564/426; 564/304
[58] Field of Search ............... 564/426, 222, 384, 389, 564/390, 397, 414, 427

[56] References Cited

U.S. PATENT DOCUMENTS

| | | | |
|---|---|---|---|
| 3,159,677 | 12/1964 | Godefroi | 564/427 X |
| 3,836,670 | 9/1974 | Freed et al. | 564/427 X |
| 4,008,277 | 2/1977 | Hewett et al. | 564/427 X |
| 4,194,009 | 3/1980 | Molloy et al. | 564/347 X |
| 4,313,896 | 2/1982 | Molloy et al. | 564/347 X |
| 4,314,081 | 2/1982 | Molloy et al. | 564/347 |

FOREIGN PATENT DOCUMENTS 41-18544 11/1966 Japan .................... 564/427

*Primary Examiner*—Robert V. Hines
*Attorney, Agent, or Firm*—Wegner & Bretschneider

[57] ABSTRACT

The present invention relates to novel biologically active tricyclic compounds, of the general formula I:

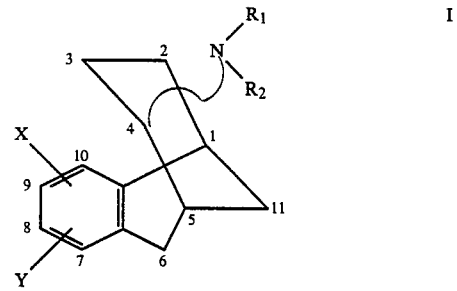

and salts thereof, in which
$R_1$ represents hydrogen, alkyl of 1–6 carbon atoms, an optionally substituted aralkyl group or an acyl group,
$R_2$ represents hydrogen, alkyl (1–6 C), or an optionally substituted aralkyl group, or
$R_1 + R_2$ together with the nitrogen atom represent a heterocyclic 5- or 6-membered ring, p1 X and Y each represent hydrogen, hydroxy, halogen, alkyl or alkoxy of 1–6 carbon atoms, nitro, $CF_3$ or an acyloxy group, and
the dotted line signifies an optional extra bond.

The compounds of the general formula I have valuable anti-depressant activity without a sustained influence on appetite.

14 Claims, No Drawings

BIOLOGICALLY ACTIVE TRICYCLIC COMPOUNDS AND PHARMACEUTICAL COMPOSITIONS CONTAINING SAME

This is a continuation of Ser. No. 886,489, filed Sept. 8, 1986, abandoned, which is a continuation of Ser. No. 772,478, filed Oct. 4, 1985; which, in turn, is a continuation of Ser. No. 545,797, filed Oct. 26, 1983; which is a continuation of Ser. No. 348,371, filed Feb. 10, 1982; which is a continuation of Ser. No. 842,882, filed Oct. 17, 1977, all abandoned.

The present invention relates to novel biologically active tricyclic compounds, to processes for the preparation of these compounds and to the pharmaceutical application of these compounds. Particularly the invention relates to novel 4-amino-benzo(b)bicyclo[3.3.1]nonene derivatives of the general formula I:

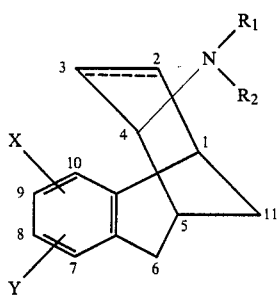

and salts thereof, in which $R_1$ represents hydrogen, alkyl of 1-6 carbon atoms, an optionally substituted aralkyl group or an acyl group, $R_2$ represents hydrogen, alkyl (1-6C), or an optionally substituted aralkyl group, or $R_1 + R_2$ together with the nitrogen atom represent a heterocyclic 5- or 6-membered ring, X and Y each represent hydrogen, hydroxy, halogen, alkyl or alkoxy of 1-6 carbon atoms, nitro, $CF_3$ or an acyloxy group, and the dotted line signifies an optional extra bond.

The compounds of the general formula I have valuable biological activities, particularly a pronounced anti-depressant activity without a sustained influence on appetite. In this respect these compounds differ essentially from related compounds known from U.S. Pat. No. 4,008,277, viz. 11-amino-benzo(b)bicylco[3.3.1]nona-3,6(10a)dienes. The latter compounds have a sustained anorectic activity and moderate anti-depressant activity, an activity-pattern which renders these compounds unfit for treating depressed individuals.

The compounds of the invention can be prepared according to methods in actual use or described in the literature for similar compounds.

The compounds of formula I, in which the dotted line signifies an extra bond, may be prepared quite conveniently by a condensation and simultaneous re-arrangement of a compound of general formula II:

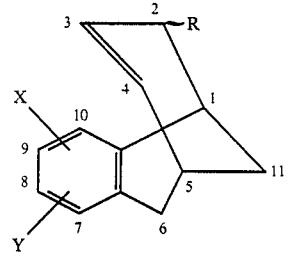

in which X and Y have the meanings above indicated and R stand for a suitable leaving group, with an amine of the general formula:

or a salt thereof, in which $R_1$ and $R_2$ have the aforesaid meanings.

The leaving group R of the starting product II is preferably halogen, such as iodine, bromine or chlorine, but also other leaving groups such as ester or ether moieties and in particular sulphonyloxy groups, e.g. a tosyloxy or mesyloxy group, may be used.

The compounds of formula I with a saturated bond at position 2 of the molecule may additionally be prepared from the corresponding unsaturated compound of formula I by hydrogenation in the presence of a suitable catalyst such as Pt, $PtO_2$, Pd/C or preferably Raney nickel.

The starting compounds of the general formula II are as far as known novel compounds. They may be prepared according to the usual methods described in the literature for similar compounds.

A very convenient starting product in the synthesis of the compounds of formula II is a substance of the general formula III or IV:

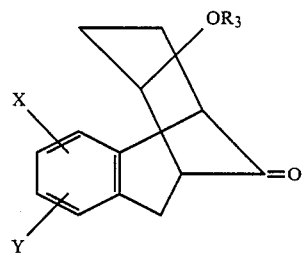

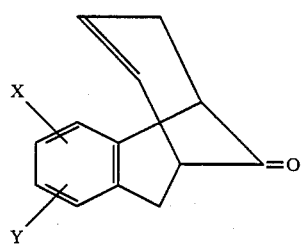

in which X and Y have the meanings indicated previously, the $R_3$ stands for hydrogen or a well-known protecting group.

The compounds III may be prepared in the usual manner starting from an optionally substituted enamine of β-tetralone. The tetralone in question is converted with acroleine into the corresponding 4-hydroxy-benzo(b)bicyclo[3.3.1]nonene-11-one. The 4-hydroxy group may additionally be protected by a well-known hydroxyl-protecting group, such as a benzyl, tetrahydropyranyl or preferably an acyl group, e.g. acetyl or benzoyl.

Sulphonylation of the 4-hydroxy group for example with tosyl- or mesylchloride, followed by removal of the sulphonyloxy group thus introduced affords a compound of the general formula IV.

The condensation of the 2-tetralone-enamine with acrolein may be carried out in the presence of a tertiary amine in a variety of solvents at temperatures between about 30° to 120° C., but preferably at the boiling point of the solvent used. The flow sheet on the next page shows briefly a method for the preparation of the product of formula II starting from a compound of formula III or IV.

A shorter and more direct method for the preparation of the compounds of formula I is starting from an α,β-unsaturated or saturated ketone of formula V:

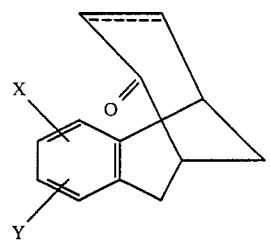

V in which X, Y and the dotted line have the meanings defined above. A starting compound of formula V may be prepared in the manner as indicated in the flowsheet.

A compound of formula I can be prepared by a reductive ammination of the ketone of formula V with formamide, N-alkylformamide, N,N-dialkylformamide or an amine of the formula $HNR'_1R'_2$, in which $R'_1$ and $R'_2$ have the same meanings as assigned to $R_1$ and $R_2$ except for an acyl group, in the presence of a reducing agent.

Flow sheet

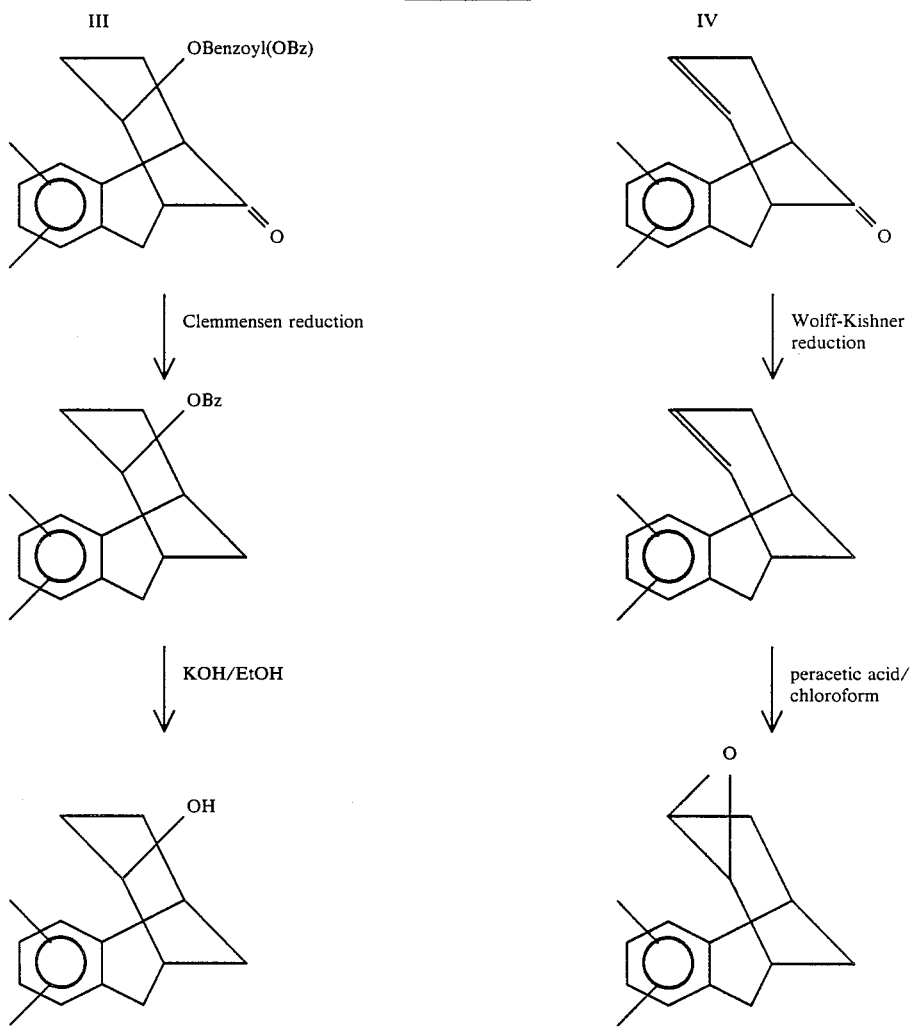

-continued
Flow sheet
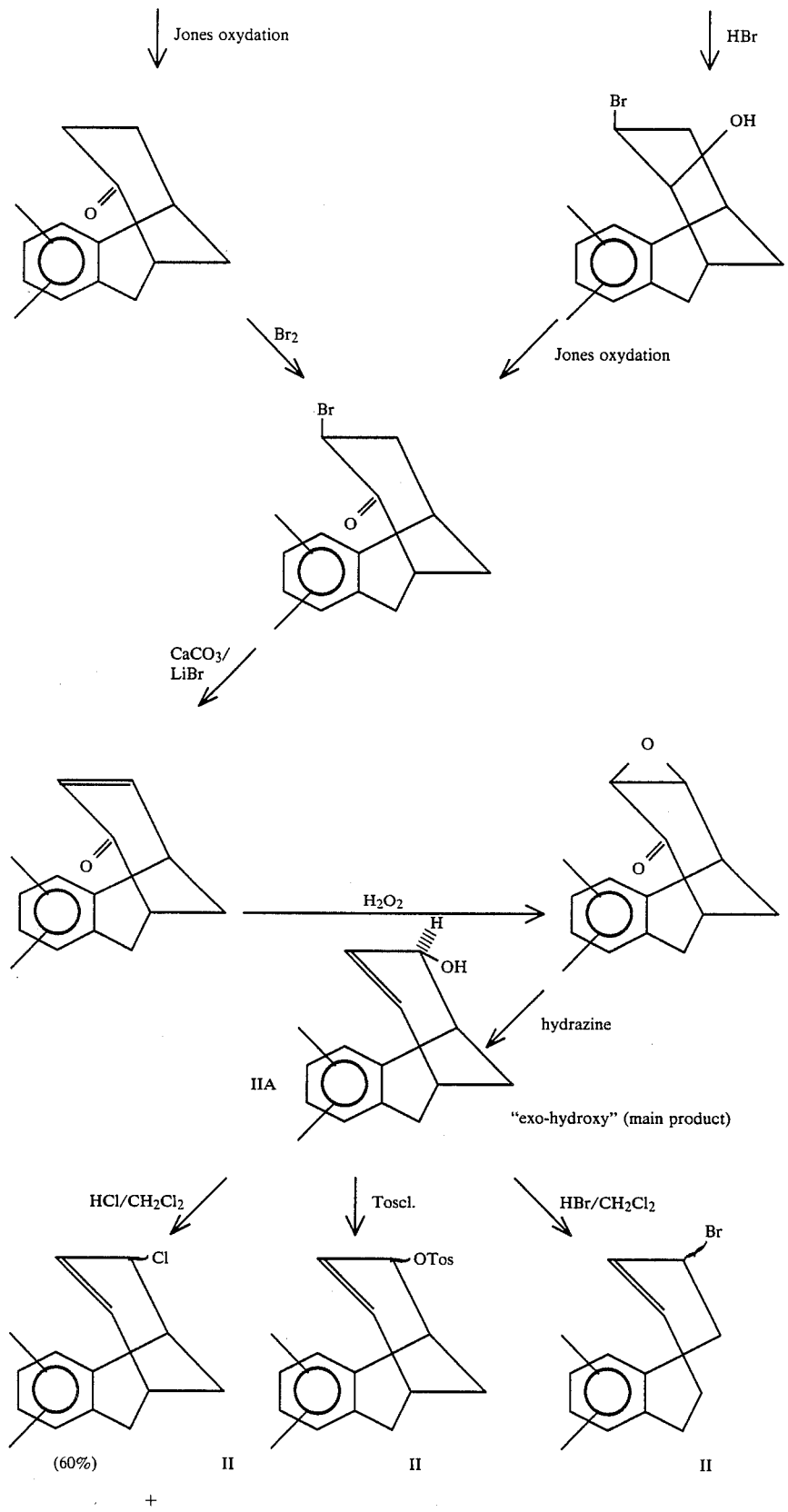

-continued
Flow sheet

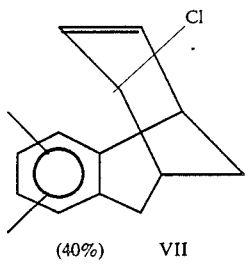

(40%)  VII

Well-known reducing agents in this connection are formic acid or formic acid derivatives (Leuckart reaction), metalhydrides, particularly complex-metalhydrides, such as lithiumaluminiumhydride, sodiumborohydride, sodiumcyanoborohydride, sodiumtrimethoxyborohydride or di-isobutylaluminiumhydride, and alkalimetals, preferably sodium, in an alcohol such as ethanol or isopropanol.

In general, a reductive ammination on the $\alpha,\beta$-unsaturated ketone of formula V (dotted line signifies extra bond) results in a mixture of the saturated and unsaturated amine of formula I. The ratio in which both components are present in the mixture strongly depends on the reducing agent used. The use of formic acid or a formic acid derivative as reducing agent yields mainly the saturated amine of formula I.

The mixture of saturated and unsaturated compounds can be separated by physical means such as crystallisation, column-chromatography, thin-layer-chromatography etc.

Where formamide or N-alkylformamide is used in the aforesaid reductive ammination, the resulting compound is in first instance a N-formyl derivative of a compound of formula I, which formyl-derivative can be hydrolysed to obtain the primary amine I or secondary amine I respectively or can be reduced in the usual manner in which case the formyl group is converted into a methyl group.

The compounds of the invention can further be obtained by a reduction of the oxime moiety of a compound of formula VI:

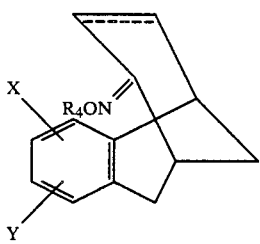

VI in which X, Y and the dotted line have the aforedefined meanings and $R_4$ represents hydrogen or a $C_1$-$C_4$ alkyl, or $C_7$-$C_{10}$ phenylalkyl group. A compound of formula VI can be prepared by the reaction of the ketone V with hydroxylamine or a hydroxylaminealkyl- or phenylalkylether.

Any reducing agent well-known for the reduction of an oxime may be applied such as hydrogen in the presence of a catalyst, metalhydrides, especially lithiumaluminiumhydride, alkalimetals, especially sodium, in a suitable solvent such as ether, benzene or alcohol or zinc dust or an alkalimetalamalgam, e.g. lithiumamalgam or sodiumamalgam in, for example, sodiumhydroxide.

This reduction yields mainly the saturated compounds of formula I.

A further method for the preparation of the compounds of formula I consists of the reaction of a compound of formula VII:

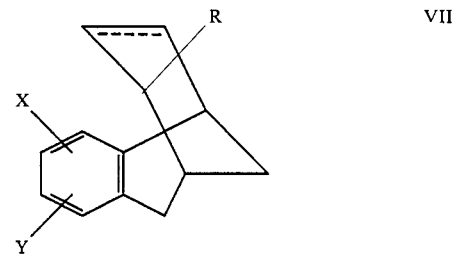

in which X, Y, R and the dotted line have the meanings defined above, with an amine of the formula $HNR_1R_2$, in which $R_1$ and $R_2$ have the meanings assigned above, or a salt thereof.

The starting compound of formula VII may be prepared in the manner indicated in the flow-sheet or from a compound of formula V by reducing the oxo-group to a hydroxyl-group, followed by converting this hydroxyl group into a well-known leaving group, as defined before. The reduction of the ketone V to the corresponding alcohol can be carried out by any reducing agent well-known for this conversion, such as hydrogen in the presence of a suitable catalyst, metalhydrides, such as lithiumaluminiumhydride, sodiumborohydride, sodiumcyanoborohydride, aluminiumhydride etc. Starting from the $\alpha,\beta$-unsaturated ketone, the corresponding $\alpha,\beta$-unsaturated alcohol can be obtained using reducing agents which mainly do not attack the conjugated double bond such as sodiumborohydride and especially aluminiumisopropoxide in isopropanol (Meerwein-Ponndorf reduction) or aluminiumhydride.

A method for preparing primary amines of formula I, especially saturated amines, which is closely related to the last-mentioned method, consists of the reduction of an azide of the formula:

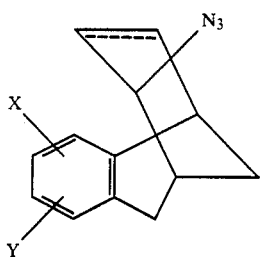

VIII in which X, Y and the dotted line have the meanings assigned above. The reduction is carried out in a manner which is well-known in the reduction of azides, for example with the aid of complex metalhydrides such as LiALH$_4$. For other reduction means reference is made to the well-known chemical textbooks.

The azide of formula VIII is prepared by the reaction of a compound of formula VII with sodium- or potassiumazide.

The aforesaid primary reactions for the preparation of the compounds of the invention (I) may be followed by additional reactions for the conversion of a compound of formula I into a functional derivative, such as a salt, or for the conversion from one compound of the invention into another compound of the invention.

So, it is possible to modify a substituent at the phenyl nucleus into another substituent within the definition of X and/or Y. For example, a methoxy group may be converted into a hydroxyl group, e.g. by treating with fused pyridine. HCl in the absence of a solvent or by hydrolysis with HBr; a hydroxy group can be converted into an alkoxy group, halogen, or an acyloxy group in a conventional manner.

The amines of the invention, unsubstituted or monosubstituted at the nitrogen atom (R$_1$ and/or R$_2$ is hydrogen), may be (ar)alkylated in the usual manner, for example by reacting the compound with an (ar)alkylhalide, or by acylating the compound followed by reduction of the carbonyl group.

For the introduction of methyl-groups at the nitrogen atom the method of Eschweiler-Clarke or the reaction with formaldehyde or haloformic esters, followed by reduction with e.g. sodiumcyanoborohydride is to be preferred.

An acyl derivative of the compounds according to the invention, in which at least one of the groups R$_1$ or R$_2$ is hydrogen may be obtained by acylating the compound in the usual manner, preferably by using an anhydride or acid halide.

All these additional conversions which can be carried out after the aforesaid primary reactions are standard procedures well-known in the art. As far as specific reagents have been mentioned in these additional conversions, it may be understood that these reagents can be replaced by other reagents, well-known in organic chemistry, having a similar effect as the specific reagents described.

The compounds of formula I possess three asymetric centres. As a result thereof a compound I may consist of a mixture of two racemic diastereoisomers of formula I, in which the amino-group is either in exo or in endo position. The racemic diastereoisomers I may be separated, if desired, by physical techniques such as fractional crystallisation, column chromatography, preparative thin-layer chromatography or counter current distribution.

The separation of diastereoisomers, however, can also be carried out in an earlier step of the synthesis, for example on the compound of formula II A indicated in the flow-sheet or on the compound of formula VII. This separation in an earlier stage of the synthesis obviously results directly in a specific (racemic) diastereoisomer of formula I.

The racemic (separate) diastereoisomers of formula I may, if desired, by resolved in the usual manner with the aid of an optically active acid e.g. (+) or (−) tartaric acid. This resolution may, however, also be carried out in an earlier stage of the synthesis. In that case the synthesis leads to an optically active compound of formula I directly.

Both the racemic or optically active diastereoisomers of formula I as well as mixtures thereof are numbered among the compounds of the invention.

The novel compounds of formula I may be isolated from the reaction mixture in the form of a pharmaceutically acceptable acid addition salt, dependent on the conditions in which the reaction is carried out. The pharmaceutically acceptable salts may also be obtained by treating the free base I with an organic or inorganic acid such as HCl, HBr, HI, H$_2$SO$_4$, H$_3$PO$_4$, acetic acid, propionic acid, glycollic acid, maleic acid, malonic acid, succinic acid, tartaric acid, citric acid, benzoic acid, ascorbic acid etc.

The term "alkyl" used in the definition of X, Y, R$_1$ and R$_2$ of the general formula I means a saturated branched or unbranched hydrocarbon radical with 1–6 carbon atoms, such as methyl, ethyl, n.propyl, n.butyl, cyclopropyl, cyclobutyl, isopropyl, isobutyl, t.butyl, n-pentyl, isopentyl, cyclopentyl and hexyl. The same applies to the alkyl group present in the term "alkoxy" used in the definition of X and Y.

By halogen is preferably meant a chloro- or bromogroup.

By an "aralkyl group", mentioned in the definition of R$_1$ and R$_2$ is meant an alkyl group with 1–6 carbon atoms, substituted with at least one aromatic group. Preferably a phenylalkyl group is meant, in which the alkyl group has 1–4 carbon atoms and in which the phenyl group may be substituted by one or more halogen, lower alkyl or alkoxy groups (1–4C), such as benzyl, phenylethyl, phenylpropyl, phenylbutyl, 1-methyl-1-phenyl-ethyl, o-, m-, or p-anisyl, o-, m- or p-chlorobenzyl, veratryl or o-, m- or p-methyl-phenethyl.

An "acyl group" mentioned in the definition of R$_1$ means a group derived from an aliphatic or aromatic carboxylic acid. The aliphatic carboxylic acids cover acids with 1–18 carbon atoms, including a carbocyclic ring, and particularly those with 1–8 carbon atoms, such as acetic acid, propionic acid, butyric acid, iso-butyric acid, valeric acid, hexanoic acid, heptanoic acid, trimethyl-acetic acid, cyclopentane carboxylic acid and cyclohexane carboxylic acid. The aromatic carboxylic acids cover unsubstituted as well as substituted aromatic carboxylic acids, with 7–18 carbon atoms, especially the optionally substituted phenyl carboxylic acids and optionally substituted phenylalkyl carboxylic acids, in which the alkyl group contains 1–4 carbon atoms and may be saturated as well as unsaturated, such as benzoic acid, o-, m- or p-toluenic acid, o- or p-chlorobenzoic acid, p-methoxybenzoic acid, phenyl-acetic acid, phenylpropionic acid, cinnamic acid, phenylbutyric acid, p-methylphenyl-acetic acid, etc.

The acyl group in the term "acyloxy" used in the definition of X and Y has a similar meaning.

The heterocyclic five- or six-membered rings, as mentioned in the definition of $R_1$ and $R_2$ (together with the nitrogen atom), are derived from cyclic amines, especially those in which at least one and no more than two hetero-atoms are present, one of which being nitrogen, the optional other one being nitrogen or oxygen, such as pyrrole, pyrroline, pyrrolidine, piperidine, pyrazole, imidazole, imidazolidine, pyrazolidine, piperazine, oxazolidine, morpholine, etc.

The compounds of the invention may be administered enterally or parenterally, preferably in a daily dosage of from 0.01–10 mg per kg body weight.

Mixed with suitable auxiliaries the compounds I may be compressed into solid dosage units, such as pills, tablets and coated tablets or be processed into capsules.

By means of suitable liquids the compounds I can also be applied as an injection preparation in the form of solutions, suspensions or emulsions.

Preferred compounds according to the invention have the general formula:

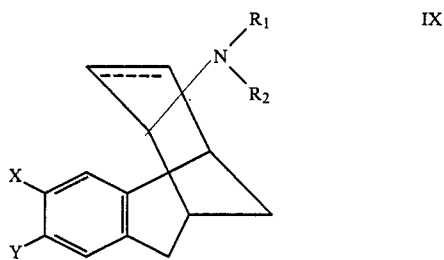

IX and salts thereof, wherein the dotted line has the meaning assigned above and in which $R_1$ and $R_2$ each represent hydrogen or alkyl (1–4C) and X and Y each represent hydrogen, halogen or alkyl (1–4C).

More particularly those compounds of formula IX are preferred, in which the dotted line signifies an extra bond, X represents hydrogen and Y represents halogen; and especially the compound of the formula:

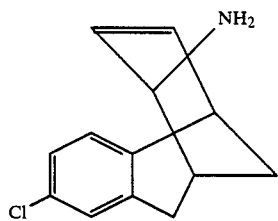

and salts thereof.

STARTING PRODUCTS

The preparation of the 8-chloro-substituted starting product according to the general formula II is described starting from 6-chloro-2-tetralone. Other starting products according to formula II are prepared in a similar manner.

A. 6-chloro-2-tetralone pyrrolidine enamine

A solution of 6-chloro-2-tetralone (260 g) in benzene (1.5 l) and pyrrolidine (208 ml) was refluxed under nitrogen for 2.5 h using a Dean and Stark water separator to collect the water formed. The reaction mixture was evaporated to dryness under reduced pressure, venting with nitrogen at the end of the distillation. The residue was triturated with hexane to give 6-chloro-tetralone pyrrolidine-enamine (276 g; 82%) m.p. 121°–122° C.

B. 8-chloro-4-hydroxy-benzo(b)bicyclo[3.3.1]nonen-11-one

B.1.
6-chloro-2-tetralone pyrrolidine enamine (390 g) was added portionwise during 10 min. to a stirred solution of acrolein (214 ml) in methylene dichloride (3.0 l) cooled to −50° to −55° C. The reaction mixture was stirred for 30 min. at −50° to −55° C., then the temperature was allowed to rise to +5° during 3 h. Water (420 ml) was added, followed by 5N hydrochloric acid (400 ml) and the resulting biphase mixture was stirred at room temperature for 2 h and set aside overnight. The layers were separated and the aqueous layer was extracted with methylene dichloride. The methylene dichloride extracts were washed with 1N hydrochloric acid, aqueous brine, dried and evaporated to dryness to give a mixture (approx. 60:40) of 8-chloro-4-exo- and 8-chloro-4-endo-hydroxy-benzo(b)bicyclo[3.3.1]nonen-11-one as an oil (371 g).

B.2.
Acrolein (389 ml) was added to a stirred solution of 6-chloro-2-tetralone (738 g) in tetrahydrofuran (738 ml) and triethylamine (738 ml) under a nitrogen atmosphere and the mixture was heated under reflux for 2.5 h.

The solvents were distilled off in vacuo and the triethylamine finally removed by azeotropic distillation with toluene (2.75 l) in portions (250 ml).

The crude ketal mixture (810 g) was dissolved in toluene, filtered through alumina, and the eluate evaporated to give a mixture (approx. 60:40) of 8-chloro-4-exo- and 8-chloro-4-endo-hydroxy-benzo(b)bicyclo[3.3.1]nonen-11-one as an oil (792 g).

C. 4-Exo- and 4-endo-benzoyloxy-8-chloro-benzo(b)bicyclo[3.3.1]-nonen-11-one A solution of 8-chloro-4-exo- and 8-chloro-4-endo-hydroxy-benzo(b)bicyclo[3.3.1]nonen-11-one (52 g) in pyridine (104 ml) was cooled with stirring to 2° and benzoyl chloride (30.5 ml) was added dropwise, keeping the temperature below 10° C. Stirring was continued at 5° to 10° C. for 3.5 h. Water was added to the cooled, stirred mixture to precipitate the product, which was dissolved in methylene dichloride and washed with 2N hydrochloric acid, water to pH 7, dried, and evaporated to give a mixture of 4-exo- and 4-endo-benzoyloxy-8-chloro-benzo(b)bicyclo[3.3.1]-nonen-11-one (62 g) (approx. 60:40).

A solution of the product in methylene dichloride was filtered through a column of alumina, concentrated, and the residue crystallised from methylene dichloride-cyclohexane to give pure 4-exo-benzoyloxy-8-chloro-benzo(b)bicyclo[3.3.1]nonen-11-one (26 g) m.p. 184°–186° C. The mother liquor was chromatographed over alumina to give a further quantity (7.5 g) of pure 4-exo-benzoyloxy-8-chloro-benzo(b)bicyclo[3.3.1]nonen-11-one (18.5 g) m.p. 120°–122° C.

D. 4-exo-benzoyloxy-8-chloro-benzo(b)bicyclo[3.3.1]nonene

Zinc wool (550 g) is amalgamated with a solution of mercuric chloride (40 g) in water (700 ml) and conc. hydrochloric acid (350 ml). The aqueous layer is decanted off and replaced with water (400 ml), conc. hydrochloric acid (600 ml), and toluene (600 ml). 4-exo-Benzoyloxy-8-chloro-benzo(b)bicyclo[3.3.1]nonen-11-one [containing 10% of 4-endo-benzoyloxy isomer] (205 g) is added to the above mixture which is then refluxed with vigorous stirring for 24 h. After cooling, the toluene layer is separated, washed three times with water, dried, and the solvent removed in vacuo to give a yellow oil (190 g). Crystallisation from light petroleum gives 4-exo-benzoyloxy-8-chloro-benzo(b)bicyclo[3.3.1]nonene, m.p. 111°–112° C.

E.
8-chloro-4-exo-Hydroxy-benzo(b)bicyclo[3.3.1]nonene

A suspension of 4-exo-benzoyloxy-8-chloro-benzo(b)bicyclo[3.3.1]nonene (105 g) in ethanol (600 ml) is refluxed with 10N potassium hydroxide (120 ml) for 1 h. After cooling, the solution is poured into water and the precipitated gum dissolved in methylene dichloride. The methylene dichloride extract is washed three times with water, dried and the solvent removed in vacuo.

Crystallisation from ether-light petroleum gives 8-chloro-4-exo-hydroxy-benzo(b)bicyclo[3.3.1]nonene (65 g), m.p. 141°–143° C.

F. 8-chloro-benzo(b)bicyclo[3.3.1]nonen-4-one

Jones reagent (90 ml) is added over 15 min. to a solution of 8-chloro-4-exo-hydroxy-benzo(b)bicyclo[3.3.1]nonene (65 g) in acetone (500 ml), maintaining the temperature below 10° C. After 30 min. the reaction mixture is fully watered out and extracted with methylene dichloride. The methylene dichloride extract is washed three times with water, dried and the solvent removed in vacuo to give 8-chloro-benzo(b)bicyclo[3.3.1]nonen-4-one as a crude yellow oil (60 g) which is brominated without further purification. A pure sample, m.p. 58°–60° C., is obtained by crystallisation from ether-light petroleum.

G.
3-Bromo-8-chloro-benzo(b)bicyclo[3.3.1]nonen-4-one

8-Chloro-benzo(b)bicyclo[3.3.1]nonen-4-one (105 g) is dissolved in a mixture of methylene dichloride (60 ml) and ether (1:1) and the solution cooled with an efficient ice/salt bath. Bromine (24.5 ml) is added to the solution and the cooling bath removed 5 min. after addition is complete. After a further 5 min. the solution becomes clear followed immediately by the precipitation of a white solid. The cooling bath is replaced for 10 min. to ensure complete precipitation of the product which is then filtered off and washed on the filter pad with cold ether, giving a white solid (120 g) which is dehydrobrominated without further purification. Recrystallisation from methylene dichloride/ether gives 3-bromo-8-chloro-benzo(b)bicyclo[3.3.1]nonen-4-one, m.p. 168°–170° C.

H.
8-Chloro-benzo(b)bicyclo[3.3.1]nona-2,6a(10a)-dien-4-one

A suspension of calcium carbonate (310 g) in dimethylacetamide (1.1 l) is heated to just below reflux, then anhydrous lithium bromide (52 g) and 3-bromo-8-chloro-benzo(b)bicyclo[3.3.1]nonen-4-one (155 g) are quickly added. After refluxing for 1½ h. with vigorous stirring, the reaction mixture is cooled, poured into water and carefully acidified with 5N hydrochloric acid to give a solid which is filtered off and dissolved in ether. The ethereal solution is washed four times with water, dried and evaporated to give a residue, which on trituration with a small volume of ether gives a buff solid (93 g). Filtration of the mother liquor material, dissolved in methylene dichloride through a short silica column followed by crystallisation gives a further crop (6 g).

Recrystallisation from methylene dichloride/ether gives 8-chloro-benzo(b)bicyclo[3.3.1]nona-2,6a(10a)dien-4-one as an off-white solid, m.p. 118°–119° C.

I.
8-Chloro-2,3-exo-epoxy-benzo(b)bicyclo[3.3.1]nonen-4-one

8-Chloro-benzo(b)bicyclo[3.3.1]nona-2,6a(10a)dien-4-one (25 g) is dissolved in methanol (325 ml) then quickly cooled to −5° C., giving a fine suspension. 4N Sodium hydroxide (18 ml) and 30% hydrogen peroxide (23 ml) are then added simultaneously over 20 min., the temperature being kept below 0° C. The cooling bath is removed and the suspension stirred for 1½ h. Water is added and stirring continued for 15 min. to give a white precipitate, which is filtered off and dissolved in methylene dichloride. The methylene dichloride solution is washed four times with water, dried, and the solvent removed in vacuo to give the product as a clear oil (23 g).

Crystallisation from ether gives 8-chloro-2,3-exo-epoxy-benzo(b)bicyclo[3.3.1]nonen-4-one (21.5 g) as prisms, m.p. 93°–94° C.

J.
8-Chloro-2-exo-hydroxy-benzo(b)bicyclo[3.3.1]nona-3,6a(10a)diene

A solution of 8-chloro-2,3-exo-epoxy-benzo(b)bicyclo[3.3.1]nonen-4-one (20 g) in methanol (200 ml) and acetic acid (1.7 ml) is quickly cooled to 0° C., giving a dense crystalline precipitate. Hydrazine hydrate (13 ml) is added over approx. 10 min., so that the temperature does not rise above 5° C. After 15 min. the reaction is watered out and the yellow gum, which is precipitated, is extracted into methylene dichloride. The methylene dichloride extract is washed three times with water, dried and solvent removed in vacuo to give the crude product as an orange oil (18 g) which is filtered through a short silica column in toluene. Crystallisation from ether/light petroleum gives 8-chloro-2-exo-hydroxy-benzo(b)bicyclo[3.3.1]nona-3,6a(10a)diene (12.3 g) as slightly yellow needles, m.p. 102°–103° C.

K. 2-Bromo-8-chloro-benzo(b)bicyclo[3.3.1]nona-3,6a(10a)diene

8-Chloro-2-exo-hydroxy-benzo(b)bicyclo[3.3.1]nona-3,6a(10a)diene (11 g) is dissolved in methylene dichloride (120 ml) and the solution saturated with hydrogen bromide gas at room temperature. After 10 min., ice-cold water is added and the organic layer separated and washed three times with further portions of ice-cold water. Removal of solvent in vacuo gives 2-bromo-8-chloro-benzo(b)bicyclo[3.3.1]nona-3,6a(10a)diene (13 g) as a brown oil, which is treated with various amines without purification.

L. 2,8-Dichloro- and 4,8-dichloro-benzo(b)bicyclo[3.3.1]nona-2,6a(10a)diene

Hydrogen chloride gas is bubbled slowly through a methylene dichloride solution of 8-chloro-2-exo-hydroxy-benzo(b)bicyclo[3.3.1]nona-3,6a(10a)diene (3 g). During a period of 30 min., the temperature of the solution is reduced from 30° C. to 0° C.; ice-cold water is then added and the methylene dichloride layer washed a further three times with water. Drying and removal of solvent in vacuo gives a mixture of 2-exo-8-dichloro-benzo(b)bicyclo[3.3.1]nona-3,6a(10a)diene and 4-exo,8-dichloro-benzo(b)bicyclo[3.3.1]nona-2,6a(10a)diene in a ratio of 3:2.

EXAMPLE I

8-Chloro-4-dimethylamino-benzo(b)bicyclo[3.3.1]nona-2,6a(10a)diene

Dimethylamine (35 ml) is added to a stirred solution of 3.5 g of 2-bromo-8-chloro-benzo(b)bicyclo[3.3.1-]nona-3,6a(10a) (oil, obtained in k.) in ether (15 ml). The mixture is stirred for 1½ h. at 0° C., then the cooling bath is removed and the amine allowed to evaporate off. Water is added to the residue which is extracted into methylene dichloride, washed three times with water, dried and solvent removed to give a crude product (3.0 g) containing the title compound as the main component. The crude product is treated with hydrogen chloride in methylene dichloride, after which the solvent is removed, and the residue triturated with ether thus removing any remaining neutral material. The residual product is regenerated from its hydrochloride salt and carefully chromatographed on alumina (100 g) eluting with toluene. Those fractions which are still mixtures are re-chromatographed, eluting with toluene/hexane (2:1). All fractions containing the pure slower running isomer are combined and reconverted to the hydrochloride salt. Recrystallisation from methanol/ether gives 8-chloro-4-exo-dimethylamino-benzo(b)bicyclo[3.3.1-]nona-2,6a(10a)diene hydrochloride (1,4 q), m.p. sublimation 225° C.

The following compounds are prepared in a similar manner:
4-exo-dimethylamino-benzo(b)bicyclo[3.3.1]nona-2,6-a(10a)diene HCl, m.p. 202°–218° C.,
8-chloro-4-exo-methylamino-benzo(b)bicyclo[3.3.1-]nona-2,6a(10a)diene HCl, m.p. 245°–260° C.,
4-exo-methylamino-benzo(b)bicyclo[3.3.1]nona-2,6a(10a)diene HCl, m.p. sublimation 180° C.,
4-exo-amino-8-chloro-benzo(b)bicyclo[3.3.1]nona-2,6a(10a)diene HCl, m.p, decomposition 225° C.,
4-exo-amino-benzo(b)bicyclo[3.3.1]nona-2,6a(10a)diene HCl, m.p. sublimation 210° C.,
4-exo-dimethylamino-8-methoxy-benzo(b)bicyclo[3.3.1]nona-2,6a(10a)diene (oil),
8-chloro-4-exo-dimethylamino-9-nitro-benzo(b)bicyclo[3.3.1]nona-2,6a(10a)diene (oil).

EXAMPLE II

4-Exo-dimethylamino-benzo(b)bicyclo[3.3.1]nona-2,6-a(10a)diene

4-Exo-chloro-benzo(b)bicyclo[3.3.1]nona-2,6a(10a)-diene (2,9 g) isolated from the mixture obtained in L, in dry tetrahydrofuran (10 ml) is heated with dimethylamine (15 ml) for 4 hours at 70° C. The mixture is evaporated and the residue taken up in methylenedichloride. The methylene chloride solution is washed with water, dried and evaporated to give a crude product (2.8 g). Chromatography on alumina (140 g), eluting with toluene/light petroleum (3:2), and isolating the slower running fraction (900 mg) yields the title compound as free base, which is converted to the hydrochloride salt in methylene dichloride. Crystallisation from methanol/ether gives 4-exo-dimethylamino-benzo(b)bicyclo[3.3.1]nona-2,6a(10a)diene hydrochloride (850 mg) as white prisms, m.p. 210°–215° C.

The following compounds are prepared in an analogous manner:
8-chloro-4-exo-dimethylamino-benzo(b)bicyclo[3.3.1-]nona-2,6a(10a)diene.HCl, m.p. sublimation 225° C.,
4-exo-methylamino-benzo(b)bicyclo[3.3.1]nona-2,6a(10a)diene.HCl, m.p. sublimation 180° C.

EXAMPLE III 4-exo-amino-benzo(b)bicyclo[3.3.1]nonene

To 0.5 g 4-exo-amino-benzo(b)bicyclo[3.3.1]nona-2,6a(10a)diene in THF (50 cc) is added 200 mg palladium (10%) on charcoal. Hydrogen is introduced through the mixture until the theoretical quantity H$_2$ has been taken up. The mixture is then filtered and the filtrate evaporated in vacuo. Yield 0.5 g of oily substance.

EXAMPLE IV 4-formamido-benzo(b)bicyclo[3.3.1]nonene

A solution of benzo(b)bicyclo[3.3.1]nonen-4-one (50 g) in a mixture of formamide (200 ml) and formic acid (100 ml) is boiled under reflux for 1½ hour and poured into a mixture of ice and potassium hydroxide solution. After allowing to stand for about 15 hours, the precipitate is filtered off, dissolved in methylenechloride, washed neutral, and chromatographed to give 4-endo-formamido-benzo(b)bicyclo[3.3.1]nonene (20 g).

The same product is obtained starting from the unsaturated ketone, benzo(b)bicyclo[3.3.1]nona-2,6a(10a)dien-4-one, in approximately the same quantity.

In an analogous manner the following formamido-derivatives are prepared:
8-chloro-4-endo-formamido-benzo(b)bicyclo[3.3.1]nonene,
9-methyl-4-endo-formamido-benzo(b)bicyclo[3.3.1]nonene,
8-methoxy-1-endo-formamido-benzo(b)bicyclo[3.3.1-]nonene,
8-hydroxy-4-endo-formamido-benzo(b)bicyclo[3.3.1-]nonene.

EXAMPLE V 4-amino-8-chloro-benzo(b)bicyclo[3.3.1]nonene

A solution of 4 g of 8-chloro-4-endo-formamido-benzo(b)bicyclo[3.3.1]nonene, obtained in Example IV, in 40 ml ethanol and 4 ml 10M potassiumhydroxide is boiled under reflux for 5 hours. The solution is concentrated and the amine precipitated by addition of an excess of water. Extraction with ether gives 4 g of 8-chloro-4-endo-amino-benzo(b)bicyclo[3.3.1]nonene as an oil; melting point HCl-salt: 240° C. (decomposition).

In an analogous manner the following compounds are obtained as an oily substance:
4-endo-amino-benzo(b)bicyclo[3.3.1]nonene;
4-endo-amino-8-methoxy-benzo(b)bicyclo[3.3.1]nonene;
4-endo-amino-8-hydroxy-benzo(b)bicyclo[3.3.1]nonene;
4-endo-amino-9-methyl-benzo(b)bicyclo[3.3.1]nonene.

EXAMPLE VI 8-chloro-4-methylamino-benzo(b)bicyclo[3.3.1]nonene

A suspension of lithiumaluminiumchloride (0.92 g) in 20 ml tetrahydrofuran is added to a solution of 3.5 g of 8-chloro-4-endo-formamido-benzo(b)bicyclo[3.3.1]nonene (Example IV) in 4 ml dioxan and the resultant mixture stirred for 5 hours at ambient temperature. After addition of 2 ml water, 1 ml 4N sodiumhydroxide and 2.5 ml water the inorganic solids are filtered off. The filtrate is concentrated, diluted with water and the product extracted into ether to give 3.5 g of the crude title compound (endo form) as an oil. The compound is further purified by column-chromatography over silica gel. Melting point HCl-salt: 196° C. (decomposition).

In an analogous manner is obtained:
4-endo-methylamino-benzo(b)bicyclo[3.3.1]nonene, as an oily substance.

EXAMPLE VII 8-chloro-4-endo-dimethylamino-benzo(b)bicyclo[3.3.1]nonene

In an analogous manner as described in Example IV 10 g of 8-chloro-benzo(b)bicyclo[3.3.1]nonen-4-one is refluxed in a mixture of 40 ml dimethylformamide and 20 ml formic acid. The resulting product is poured into a mixture of ice and potassiumhydroxide solution. The alkaline mixture is extracted with methylenedichloride and the methylenedichloride layer is washed, dried and evaporated to dryness. The oily substance obtained (6.5 g) is converted into the HCl-salt; m.p. 192° C. (decomposition).

EXAMPLE VIII 8-chloro-4-exo-amino-benzo(b)bicyclo[3.3.1]nonene

To 0.5 g 8-chloro-4-endo-mesyloxy-benzo(b)bicyclo[3.3.1]nonene, (m.p. 206°–208° C.) obtained from the corresponding 4-endo-hydroxy compound (m.p. 88°–92° C.) by reaction with mesylchloride, are added 3 ml dimethylformamide and 0.2 g of sodium-azide. The mixture is refluxed for 5 hours and then poured into water, after which it is extracted with methylenedichloride. The methylenedichloride layers are dried and evaporated to dryness, resulting in 0.4 g of oily substance, 8-chloro-4-exo-azido-benzo(b)bicyclo[3.3.1]nonene.

The oil is added to a suspension of 300 mg LiALH$_4$ in dry ether. The mixture is refluxed for 1 hour and then cooled down. 1.2 ml Water is added dropwise to the mixture, after which it is filtered and the filtrate evaporated to dryness. Yield 0.3 g of an oily substance. M.p. HCl-salt: 200° C. (decomposition).

EXAMPLE IX 8-chloro-4-exo-dimethylamino-benzo(b)bicyclo[3.3.1]nonene

A solution of 1.25 g 8-chloro-4-exo-amino-benzo(b)bicyclo[3.3.1]nonene in a mixture of 1.2 ml formic acid and 1 ml formalin is heated at 90°–100° C. for 1 hour, and then diluted with water and a slight excess of potassium hydroxide solution. The mixture is extracted with ethylene dichloride to give 1.2 g of the oily title product. The oil is converted into the HCl-salt: m.p. 230° C. (decomposition).

The same compound is obtained by reacting dimethylamine with 8-chloro-4-endo-mesyloxy-benzo(b)bicyclo[3.3.1]nonene.

EXAMPLE X 8-chloro-4-exo-methylamino-benzo(b)bicyclo[3.3.1]nonene 3 g of 8-chloro-4-exo-amino-benzo(b)bicyclo[3.3.1]nonene, 20 ml of formic acid and 20 ml formamide are refluxed for ¾ hr. and then cooled down and poured in water. The mixture is extracted with methylenedichloride, and the methylenedichloride fraction is washed with water, dried and evaporated to dryness resulting in 2.5 g of an oily substance (8-chloro-4-formamido derivative), $R_f$ in dichloro-ethane:methanol:water (95:5:0.2)=0.82 on SiO$_2$. This oil (0,2 g) in 20 ml THF is added to 320 mg of LiALH$_4$ in 20 ml THF and processed in a manner analogous to the second step of the process of Example VIII. Yield 2 g of the oily 8-chloro-4-exo-methylamino derivative; m.p. HCl-salt 250° C.

We claim:
1. A compound of the formula:

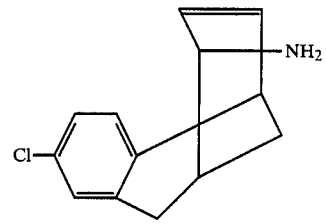

or a pharmaceutically acceptable salt thereof.

2. A pharmaceutical composition having anti-depressive properties without a sustained influence on appetite comprising an anti-depressant effective amount of a compound of the formula:

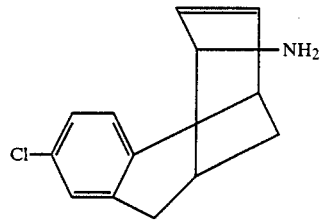

or a pharmaceutically acceptable salt thereof, and a pharmaceutically effective carrier therefor.

3. A compound of the formula:

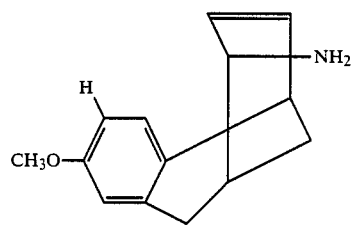

or a pharmaceutically acceptable salt thereof.

4. A pharmaceutical composition having anti-depressive properties without a sustained influence on appetite, comprising an anti-depressant effective amount of a compound of the formula:

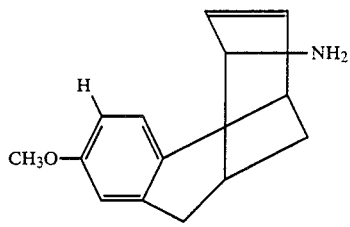

or a pharmaceutically acceptable salt thereof, and a pharmaceutically effective carrier therefor.

5. A compound of the formula:

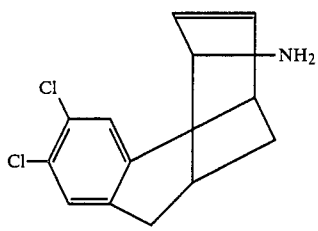

or a pharmaceutically acceptable salt thereof.

6. A pharmaceutical composition having anti-depressive properties without a sustained influence on appetite comprising an anti-depressant effective amount of a compound of the formula:

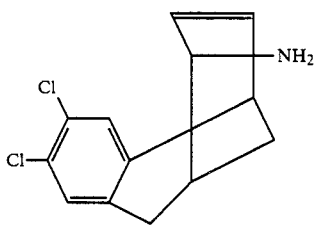

or a pharmaceutically acceptable salt thereof, and a pharmaceutically effective carrier therefor.

7. A compound of the formula:

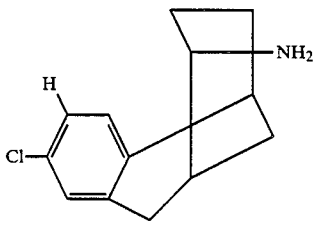

or a pharmaceutically acceptable salt thereof.

8. A pharmaceutical composition having anti-depressive properties without a sustained influence on appetite, comprising an anti-depressant effective amount of a compound of the formula:

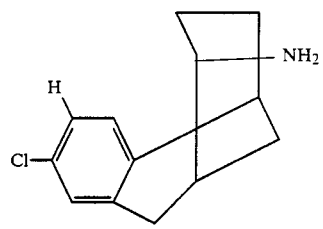

or a pharmaceutically acceptable salt thereof, and a pharmaceutically effective carrier therefor.

9. A compound of the formula:

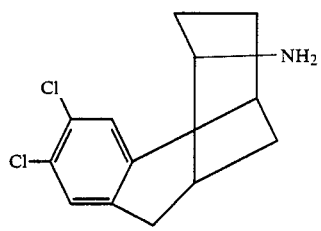

or a pharmaceutically acceptable salt therefor.

10. A pharmaceutical composition having anti-depressive properties without a sustained influence on appetite comprising an anti-depressant effective amount of a compound of the formula:

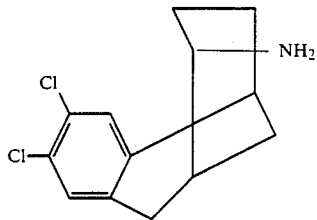

or a pharmaceutically acceptable salt thereof, and a pharmaceutically effective carrier therefor.

11. A compound of the formula:

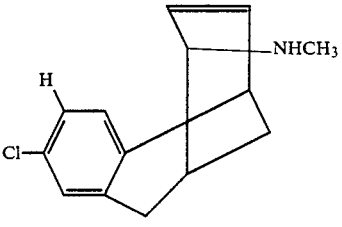

or a pharmaceutically acceptable salt thereof.

12. A pharmaceutical composition having anti-depressive properties without a sustained influence on appetite comprising an anti-depressant effective amount of a compound of the formula:

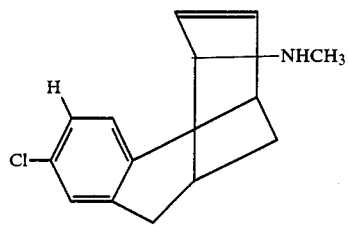

or a pharmaceutically acceptable salt thereof, and a pharmaceutically effective carrier therefor.

13. A compound of the formula:

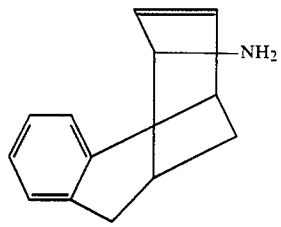

or a pharmaceutically acceptable salt thereof.

14. A pharmaceutical composition having anti-depressive properties without a sustained influence on appetite comprising an anti-depressant effective amount of a compound of the formula:

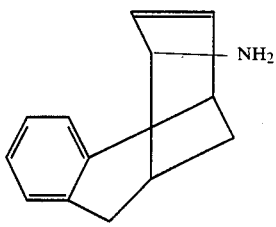

or a pharmaceutically acceptable salt thereof, and a pharmaceutically effective carrier therefor.

* * * * *